United States Patent [19]

Halderit et al.

[11] Patent Number: 5,556,890
[45] Date of Patent: Sep. 17, 1996

[54] RECLAIMING ε-CAPROLACTAM FROM CARPET WASTE

[75] Inventors: Antoon H. T. Halderit, Echt; Martin Booij, Sittard; Jan A. J. Hendrix, Born; Yvonne H. Frentzen, Venlo, all of Netherlands

[73] Assignee: DSM N.V., Netherlands

[21] Appl. No.: 253,010

[22] Filed: Jun. 2, 1994

[30] Foreign Application Priority Data

Jun. 4, 1993 [NL] Netherlands .............................. 9300963

[51] Int. Cl.$^6$ ...................... C07D 201/12; C07D 201/16; C08J 11/14
[52] U.S. Cl. .......................... 521/49.8; 521/40.5; 540/540
[58] Field of Search .................................. 521/49.8, 40.5; 540/540

[56] References Cited

U.S. PATENT DOCUMENTS

| | | | |
|---|---|---|---|
| 4,563,308 | 1/1986 | Plantema et al. | 540/540 |
| 5,032,684 | 7/1991 | Neubauer et al. | 540/540 |
| 5,169,870 | 12/1992 | Corbin et al. | 521/49.8 |

FOREIGN PATENT DOCUMENTS

| | | |
|---|---|---|
| 160312 | 10/1975 | Czechoslovakia . |
| A12440243 | 3/1976 | Germany . |
| 1253716 | 11/1977 | Germany . |
| 52-108991 | 9/1977 | Japan . |
| 53-132585 | 11/1978 | Japan . |
| 1121801 | 5/1989 | Japan . |
| 1167807 | 7/1989 | Japan . |
| 1172997 | 12/1969 | United Kingdom . |
| 1271041 | 4/1972 | United Kingdom . |

OTHER PUBLICATIONS

Abstract for German DD—75083, "Lactam Purification by Distillation, Hydrogenation, Concentration and Rectification".

J. Stresink & J. Mokry, Feasibility of Purifying 6–Caprolacctum by Hydrofining and Ion Exchange Resins, Petrochemica, 20(5/6) 171–177 (1980).

*Primary Examiner*—Frederick Krass
*Attorney, Agent, or Firm*—Cushman Darby & Cushman, L.L.P.

[57] ABSTRACT

The present invention is for a method of preparing purified ε-caprolactam from carpet waste containing nylon-6. Contaminated ε-caprolactam is obtained by depolymerizing nylon-6 from carpet waste. A mixture of the contaminated ε-caprolactam and water is then hydrogenated in the presence of hydrogen and a hydrogenation catalyst in order to produce purified ε-caprolactam. The amount of contaminated ε-caprolactam in the mixture can be between 10 and 95% by weight.

14 Claims, No Drawings

RECLAIMING ε-CAPROLACTAM FROM CARPET WASTE

BACKGROUND OF THE INVENTION

1. Technical Field

The present invention relates to the reclamation of ε-caprolactam from carpet waste, and more particularly to a method of purifying contaminated ε-caprolactam dissolved in water, in which the contaminated ε-caprolactam has been obtained by means of depolymerization of nylon-6 originating from carpet waste.

2. Background Information

U.S. Pat. No. 5,169,870, discloses a method in which nylon-6 from carpet made from nylon-6 fibers is depolymerized in the presence of phosphoric acid and steam. The phosphoric acid serves as a depolymerization catalyst. The carpet is traditionally composed of nylon-6 tufts and of a jute, polypropylene or latex backing. The backing may also contain fillers and the post-consumer carpet will also contain various sorts of dirt. These materials are present during depolymerization, due to the difficulty of fully separating the nylon-6 from the non-nylon-6 material. The non-nylon-6 material will result in impurities which have to be removed from the ε-caprolactam in order to obtain ε-caprolactam reusable for making nylon-6.

According to U.S. Pat. No. 5,169,870, this so-called "carpet" ε-caprolactam should be purified in the following manner. The volatile components and added steam which are released during depolymerization are condensed and fractionated to separate some non-aqueous contamination from this crude mixture containing water and ε-caprolactam. This crude water and ε-caprolactam mixture is then further purified by adding potassium permanganate as an oxidative treatment in order to oxidize the impurities which are not removed by the fractionation.

The addition of potassium permanganate is disadvantageous because solid manganese dioxide ($MnO_2$) is produced during the purification. Solid manganese dioxide then has to be removed from the reaction by means of, for example, filtration. The removal of manganese dioxide is troublesome, particularly in a continuous process. A further disadvantage of the process disclosed in U.S. Pat. No. 5,169,870 is that manganese dioxide is a by-product of relatively little value and causes environmental pollution.

It is known per se to purify mixtures containing water and ε-caprolactam by means of hydrogenation. EP-A-411455, CS-A-160312 and J. Stresinka and J. Mokry, PetraChemia, 20 No. 5–6, 171–177 (1970), the entire contents of which are hereby incorporated by reference, describe a process for purification of ε-caprolactam by means of hydrogenation of an ε-caprolactam/water mixture. The ε-caprolactam as described in these references is, however, obtained via the Beckmann rearrangement of cyclohexanone oxime in fuming sulphonic acid (hereafter called "rearrangement" ε-caprolactam).

Hydrogenation has never been considered as a suitable method for purification of ε-caprolactam obtained by depolymerization of nylon-6 fibers. This consideration was based on the fact that ε-caprolactam obtained by depolymerization of nylon-6 fibers contains another kind of contamination due to the additives present in nylon-6 fibers (such as lubricants, anti-statics, anti-stain compounds, dye stuffs and flame retardants) as, for example, described in JP-A-52108991.

Another reason why more contamination is present in ε-caprolactam obtained by depolymerization compared to "rearrangement" ε-caprolactam is because the depolymerization reaction is, as a rule, conducted at higher temperatures compared to the temperature of the rearrangement reaction. Higher temperature results in more side reactions of the ε-caprolactam resulting in a higher degree of contamination.

In addition, "carpet" ε-caprolactam will contain even more contaminants due to the non-nylon-6 materials (additives and backing) and dirt present in the used carpets. Because of the presence of these contaminations, "carpet" ε-caprolactam has been purified with an oxidizing agent, preferable with $KMnO_4$, a purification method described, for example, in JP-A-52108991 and JP-A-52111585, the entire contents of which are hereby incorporated by reference, for ε-caprolactam from nylon-6. This is also clear form DE-C-851195, the entire content of which is hereby incorporated by reference, which teaches that ε-caprolactam obtained from heavily contaminated nylon-6 sources will have to be purified with $KMnO_4$. It is, therefore, surprising and unexpected that hydrogenation can be used advantageously as described below for treating "carpet" caprolactam.

SUMMARY OF THE INVENTION

The object of this invention is to provide a method of purifying contaminated ε-caprolactam obtained from carpet waste in which the quality of the final product, ε-caprolactam, is at least as good as that of the ε-caprolactam obtained by the known method described above but which method does not result in the production of solid manganese dioxide.

This object is achieved in that the mixture of water and the contaminated ε-caprolactam is hydrogenated in the presence of hydrogen and a hydrogenation catalyst.

Specifically, the present invention is for a method of purifying ε-caprolactam from carpet waste containing nylon-6, comprising the steps of depolymerizing nylon-6 in order to obtain contaminated ε-caprolactam; hydrogenating a mixture of water and the contaminated ε-caprolactam in the presence of hydrogen and a hydrogenation catalyst in order to obtain purified ε-caprolactam; and recovering the purified ε-caprolactam from the mixture.

More specifically, the present invention is for a method of purifying ε-caprolactam from carpet waste containing nylon-6, comprising the steps of depolymerizing nylon-6 in order to obtain contaminated ε-caprolactam; extracting the contaminated ε-caprolactam with an organic solvent; hydrogenating a mixture of water and the contaminated ε-caprolactam in the presence of hydrogen and a hydrogenation catalyst in order to obtain purified ε-caprolactam; subjecting the mixture to ion exchange treatment in order to obtain further purified ε-caprolactam; distilling the further purified ε-caprolactam; and recovering the further purified ε-caprolactam.

It has been found that contaminated ε-caprolactam purified by the method of the present invention has the same or better properties or quality features as ε-caprolactam obtained by the method described in U.S. Pat. No. 5,169,870, the entire content of which is hereby incorporated by reference. These properties or quality features are, for example, °Hazen (ISO 8112), PM number, Abs 290 (ISO 7059), Alkalinity, V1 bases (ISO 8661) and PAN (8660).

An additional advantage of the process according to the present invention is that hydrogen is easier to obtain and to process than potassium permanganate. The method according to the present invention, therefore, also offers an economically and also environmentally attractive process for reclaiming ε-caprolactam from carpet waste.

Another advantage of the process according to the present invention is as follows. When starting with different types of nylon-6 containing carpets, ε-caprolactam, obtained from some carpets and purified with $KMnO_4$ according to the method described in U.S. Pat. No. 5,169,870 shows a visual turbidity (hazy shine in contrast with the normally observed water clear solution) when dissolved in water. This turbidity indicates impurities which make the ε-caprolactam not suitable for further reuse in making nylon-6 fiber. The turbidity also makes it impossible to measure the extinction at 290 nm according to ISO 7059.

The origin of the turbidity is found in the presence of different mixtures of non-nylon-6 material/compounds present in the carpet (waste), for example, lubricants, antistatic compounds, dye stuffs, anti-stain compounds, flame retardants and backing material. Because some carpets give rise to this turbidity and others do not, and because it is desirable to process all post-consumer nylon-6 containing carpets in a single process, the turbidity problem may arise randomly when purifying ε-caprolactam obtained from these nylon-6 containing carpets. This turbidity problem does not occur when the ε-caprolactam is prepared by the hydrogenation process of the present invention. Instead, a water clear solution is obtained. Thus, with the process of the present invention, all nylon-6 containing carpets can be used as a nylon-6 source without such a turbidity problem.

DETAILED DESCRIPTION OF THE PREFERRED EMBODIMENTS

The hydrogenation method of the present invention can be carried out in any way known to those skilled in the art. Hydrogenation is usually carried out in the presence of a heterogeneous hydrogenation catalyst. The heterogeneous catalyst can be contacted with the hydrogen-containing reaction mixture in various ways. Hydrogenation may, for example, take place in a stirred tank in which the catalyst particles are suspended in a mixture to be purified (slurry phase process). A drawback of the slurry phase process is that the catalyst particles and the purified mixture must be separated in an additional process step after the hydrogenation reaction. Such a separation step, for example, by means of filtration, is cumbersome. Therefore, hydrogenation is more preferably effected in a fixed-bed reactor with the catalyst being fixed in the reactor, so that the additional step for separation of the catalyst and reaction mixture can be omitted from the process. An example of a possible fixed-bed reactor is the trickle-phase reactor.

The hydrogenation catalyst may be any known heterogeneous hydrogenation catalyst. Examples of such catalysts are ruthenium on aluminum oxide, rhodium on aluminum oxide, platinum on carbon, palladium on carbon, Raney nickel or nickel on silicone oxide. Preferably, the hydrogenation catalyst contains nickel.

Suitable nickel catalysts with a support usually have a nickel content between about 5 and about 80 wt. %. In addition to nickel, the catalyst may contain activators such as Zr, Mn, Cu or Cr. The activator content is generally between about 1 and about 20 wt. %.

If palladium-containing heterogeneous catalysts are used, the palladium content will generally be between about 0.01 and about 10 wt. %.

If a fixed-bed reactor is used, catalysts are employed in which an active metal is on the external surface of a support. Such catalysts can be prepared using the method in which a pre-formed support (for instance, pellets, spheres or ribbons) is contacted with an aqueous solution of a metal salt (for example, the metal nitrate), dried, and subsequently calcined.

The size of the pre-formed support that is chosen will be as small as possible without the pressure drop across the fixed bed becoming unacceptable. For example, the average particle diameter of pellets for a support is usually between about 1 and about 5 mm.

Catalyst activation, if applied, can be effected in any known manner. In Example 3 of EP-A-411455, for instance, the catalyst is activated by passing gaseous hydrogen over the catalyst for 8 hours while increasing the temperature stepwise from 80° to 200° C. The activation can also be carried out in situ at a temperature of 70°–100° C. in which the catalyst is contacted with water (or a water/ε-caprolactam mixture) in which hydrogen is dissolved. The activation pressure may be between 0.1 and 10 MPa.

The hydrogenation residence time depends on the method that is chosen for contacting the heterogeneous catalyst with hydrogen and the water/ε-caprolactam mixture. If a reactor is chosen in which the catalyst is fixed in the reactor (fixed-bed reactor), the residence time is generally more than 10 seconds, and in particular more than 30 seconds, and in general the residence time is less than 10 minutes and in particular less than 7 minutes.

The required amount of heterogeneous hydrogenation catalyst in case a slurry phase process is used can easily be determined by those skilled in the art and is usually between about 0.01 and about 5% by weight of the total reaction mixture.

The amount of ε-caprolactam in the mixture to be purified may vary between about 10 and about 95% by weight. Preferably, this concentration is between about 30 and about 75% by weight of the constituents of depolymerized material.

During the hydrogenation, the hydrogen pressure is between about 0.1 and about 10 MPa and is preferably between about 0.2 and about 2 MPa. During the hydrogenation, the temperature is usually between about 20° and about 160° C.

Optionally, the mixture can be hydrogenated by first saturating the mixture with hydrogen and then bringing the saturated mixture into contact with the hydrogenation catalyst under hydrogenation conditions. The catalyst is preferably a metal on a heterogeneous support as described above. The reactor is preferably a packed-bed reactor over which the hydrogen saturated ε-caprolactam/water mixture is continuously fed. Under reaction conditions, the degree to which the hydrogenation reaction mixture is saturated with hydrogen is generally 50–100%. Preferably, the degree of saturation of the reaction mixture is 80–100%.

The nylon-6 containing carpet waste used in the process according to the present invention is normally composed of nylon-6 tufts on a backing of jute, polypropylene, latex or nylon-6 and fillers like calcium carbonate, clay and hydrated aluminum oxide. The nylon-6 carpet waste may be industrial nylon-6 carpet waste obtained as waste in the production of the nylon-6 containing carpets. The process according to the present invention is particularly suitable for post-consumer nylon-6 carpet waste, as explained above. Mixtures of industrial- and post-consumer nylon-6 containing carpet waste may also be used. The mixture of carpet waste may also contain small amounts of polyethylene terephthalate (PET), nylon-6,6, wool, cotton and other materials which are used for face fiber applications in carpets due to imperfection of the sorting procedure when collecting post-consumer carpets.

The carpets can be pretreated mechanically reducing the carpet to a smaller size. A large portion of any non-nylon-6 material, including the above mentioned backing materials, may be removed in a separator. Examples of suitable mechanical separators are those supplied by the Schirp Corporation as Type 75, Type 38CIII, Type 58, Type 38CII, Type 66, Type 71, Type 66-L, Type 57, Type 67S600, Type 64 and Type 62C. After this pretreatment, the fraction containing mainly nylon-6 material can be fed into the depolymerization reaction.

The depolymerization reaction can be carried out with or without a catalyst. In JP-A-53143585, for example, an uncatalyzed depolymerization is described, in which nylon-6 is depolymerized in the presence of superheated steam. However, depolymerization is usually carried out in the presence of a catalyst. Examples of catalyzed depolymerizations are also described in JP-A-53132585, the entire content of which is hereby incorporated by reference. Suitable catalysts are, for example, inorganic acids, including phosphoric acid and boric acid or organic acids, including benzenesulphonic acid, phthalic acid, adipic acid, and acetic acid. Phosphoric acid is in practice the most preferred.

The depolymerization is usually carried out at a temperature of between about 230° to about 325° C. and preferably between about 250° to about 280° C. The superheated steam is preferably fed to the reactor at a temperature of between about 250° to about 500° C. The steam is preferably supplied from the beginning of the depolymerization in order to take up the volatile $\epsilon$-caprolactam formed so as to obtain a condensate containing from 1 to 40% by weight of $\epsilon$-caprolactam. The content of phosphoric acid in the depolymerization reactor is usually between about 0.1 to about 10 wt. % and, preferably, between about 2 to about 7 wt. %, based on the total nylon-6 fed to the reactor.

The mixture of water and crude $\epsilon$-caprolactam, obtained after the depolymerization, can be submitted immediately to the hydrogenation step. According to the present invention, preferably one or more additional purification steps are carried out before or after the crude water/$\epsilon$-caprolactam mixture is purified by hydrogenation. A possible additional purification step which can be carried out before the hydrogenation step is a distillation step in which by-products released or formed during the depolymerization can be removed, as is described in U.S. Pat. No. 5,169,870. Another additional purification step is a purification via an ion exchanger, as for example described in JP-A-52108991 and by J. Stresinka and J. Mokry, PetraChemia, 20 No. 5–6, 171–177 (1970). Other purification steps known to those skilled in the art, such as, for example, extraction and/or absorption over active carbon, can also be applied.

As a final purification step, the $\epsilon$-caprolactam is recovered by separating it from the water, the final, purified $\epsilon$-caprolactam being obtained. This separation can be carried out in any way known to those skilled in the art. The $\epsilon$-caprolactam may, for example, be recovered by means of crystallization or hot melt crystallization. Another known method is distillation or concentration by evaporation, preferably in the presence of a small amount of sodium hydroxide solution.

It has been found that a purification process which includes (1) an extraction step with an organic solvent, (2) a hydrogenation step according to the present invention, (3) an ion exchange treatment step and (4) a final distillation step will result in $\epsilon$-caprolactam which can be directly reused in making nylon-6 suitable for making carpet fibers or any other application. Preferably the purification process is conducted in the above given sequence.

The extraction step can be conducted in the same manner as in the purification process for "rearrangement" $\epsilon$-caprolactam. Suitable extraction organic solvents are those practically immiscible with water. Examples of these solvents are ethers, for example, ethyl-, n-propyl-, butylether, dioxane; aromatic solvents, for example, benzene, toluene, xylene, cumene and ethylbenzene; aliphatic solvents, for example, cyclohexane, isopropylcyclohexane and ethylcyclohexane; chloroalkanes, for example, chloroform, mono-, di-, tri-, tetrachloro-ethane.

The ion exchange treatment step can be conducted in the same manner as in the purification process for "rearrangement" $\epsilon$-caprolactam, as described in the above mentioned references. Preferably a cationic exchanger is used first and subsequently an anionic exchanger is used.

The final distillation step can be conducted in the same manner as in the purification process for "rearrangement" $\epsilon$-caprolactam.

The present invention is explained further by reference to the following, non-restrictive examples.

EXAMPLE I

A mixture of 570 g of nylon-6 fiber and 30 g non-nylon-6 carpet waste, mechanically separated from industrial carpet waste (carpet waste: nylon-6 face fiber, latex adhesive, polypropylene backing and $CaCO_3$), was depolymerized in a Hastalloy C steel reactor in the presence of 21 ml of 85 wt. % aqueous phosphoric acid. Superheated steam was passed through the mixture for 120 min and the temperature was held at 280°–290° C. during the reaction. 3800 g of distillate was collected and was composed of 15% by weight of $\epsilon$-caprolactam, most of the remainder being composed of water. The mixture was concentrated by evaporation to a lactam concentration of 30%.

300 g of this concentrated mixture (the mixture to be purified) was introduced into a 0.5 l stirred autoclave together with 0.4 g of Raney nickel catalyst slurry (50% by weight Raney Ni in water). The mixture was hydrogenated for 1 hour under a hydrogen pressure of 0.5 MPa at 90° C. and at 900 rpm.

Most of the catalyst was then removed by means of decantation and the small amount of residual catalyst was removed by means of filtration through a fluted filter.

5 ml of 50% by weight sodium hydroxide solution was then added to the mixture which had been freed of catalyst. This mixture was then distilled by reducing the pressure in steps. Lactam was distilled at approximately 0.13–0.2 KPa. Various properties of the distilled $\epsilon$-caprolactam are shown in Table 1.

Comparative Experiment A

The mixture to be purified from Example I was diluted to a 15% by weight solution. 333 g of this mixture was stirred for 30 min together with 33.6 g of 3% by weight potassium permanganate solution at 40° C. and a pH of 7.0. The pH was adjusted to a pH of 7.0 during the oxidation with the aid of 1.0N sulphuric acid. The manganese dioxide ($MnO_2$) formed was then removed from the reaction product by means of pressure filtration. The filtration time was 35 min. The dried filter cake, predominantly composed of manganese dioxide, weighed 1.7 g.

The ε-caprolactam-containing mixture was then distilled in the same way as described in Example I. The properties of the ε-caprolactam formed in this way are shown in Table 1.

Comparative Experiment B 333 g of the mixture to be purified from Example I was immediately distilled in the same way as in Example I. The properties of the ε-caprolactam purified in this manner are shown in Table 1.

TABLE 1

|  | I | A | B |
|---|---|---|---|
| °Hazen[1] (ISO 8112) | 1 | 1 | 26 |
| PM number[2] | >10,000 | >10,000 | 177 |
| Abs 290[3] (ISO 7059) | 0.04 | 0.51 | 3.32 |
| Alkalinity[4] | 0.01 | 0.04 | 0.50 |
| Vl bases[5] (ISO 8661) | 0.08 | 0.38 | 0.61 |

[1]°Hazen is a measure of the color; a lower number implies a higher quality product.
[2]PM number (permanganate number) is a measure of the oxidizability. A higher number indicates that less oxidizable contamination is present.
[3]Abs 290 is the absorbance at 290 nm of a 50%-strength solution in a 4 cm cuvette; a lower number implies a higher quality.
[4]Alkalinity/acidity: (meq/kg) measured by titration.
[5]Vl bases: volatile bases, meq/kg, (volatile components which can be liberated with hydroxide solution).

The permanganate (PN) number is defined as the number of seconds elapsing after the addition of 1.00 ml of potassium permanganate, 0.0020 Mol/l, to ml of caprolactam solution, 3.00 g/100 ml, of K (=20° C.) until the moment at which the color of this solution becomes equal to the color of a standard solution. The standard solution consists of 3000 mg of cobalt nitrate $(Co(NO_3)_2.6H_2O)$ and 12 mg of potassium dichromate in 1 l of water. The PN number can be used for comparison of the results from the Experiments and Examples as described below.

EXAMPLE II 400 g of nylon-6 industrial carpet fiber waste was depolymerized in a Hastalloy C steel reactor in the presence of 14.7 g of 85 wt. % aqueous phosphoric-acid. Superheated steam was passed through the mixture for 155 min and the temperature was held at 280°–295° C. during the reaction. 4360 g of distillate was collected.

The distillate was composed of 8% by weight of ε-caprolactam, most of the remainder being water. The mixture was concentrated by evaporation to a lactam concentration of 33 wt. %. The resulting concentrate was the mixture to be purified.

300 g of this concentrated mixture was introduced into a 0.5 l stirred reactor together with 1.0 g of Raney nickel catalyst slurry (50% by weight Raney Ni in water). The mixture was hydrogenated for 1 hour under a hydrogen pressure of 0.1 MPa at 90° C. and at 900 rpm.

Most of the catalyst was then removed by means of decantation and the small amount of residual catalyst was removed by means of filtration through a fluted filter.

5 ml of 1.5N sodium hydroxide solution was then added to the mixture which had been freed of the catalyst. This mixture was then distilled by reducing the pressure in steps. Lactam was distilled at approximately 0.13–0.2 KPa. The properties of the distilled ε-caprolactam are shown in Table 2.

Comparative Experiment C

The mixture to be purified from Example II was concentrated by evaporation to a 70 wt. % solution. 140 g of this mixture was stirred for 15 min together with 13.3 g of 3% by weight aqueous potassium permanganate solution at 40° C. and at a pH of 7.0. The pH was kept at 7.0 during the oxidation with 1.0N sulphuric acid. The manganese dioxide $(MnO_2)$ formed was then removed from the reaction by means of pressure filtration. The filtration time was 60 min. The dried filter cake, predominantly composed of manganese dioxide, weighed 2 g.

The ε-caprolactam-containing mixture was then distilled in the same way as described in Example I. The properties of the ε-caprolactam formed in this way are shown in Table 2.

TABLE 2

|  | II | C |
|---|---|---|
| °Hazen (ISO 8112) | 4 | 53 |
| PM number | 2700 | 900 |
| Abs 290 (ISO 7059) | 0.98 | n.m[2] |
| PAN (ISO 8660)[1] | 8.3 | 9.5 |
| Turbidity[3] | no | yes |

[1]PAN number is a measure for the amount of oxidizable contamination in the ε-caprolactam. A low number indicates a low amount of contamination.
[2]n.m. = not measurable due to turbidity according to ISO 7059.
[3]measured by visual observation.

EXAMPLE III 400 g (of which 32 g were non-nylon-6 material) of nylon-6 fiber (post-consumer nylon-6 containing carpet waste originating from latex-jute, polypropylene containing carpets) mechanically separated as well as possible from carpet waste, was depolymerized in a Hastalloy C steel reactor in the presence of 15.2 ml of 85 wt. % aqueous phosphoric acid. Superheated steam was passed through the mixture for 170 min and the temperature was held at 280°–300° C. during the reaction. 5060 g of distillate was collected. The distillate was composed of 6 wt. % of ε-caprolactam, most of the remainder being water. The mixture was concentrated to a ε-caprolactam concentration of 33 wt. %. The concentrate was the mixture to be purified.

300 g of this concentrated mixture was introduced into a 1.0 l stirred reactor together with 150 g benzene. The resulting mixture was stirred for 15 minutes and subsequently two phases, a "water phase" and a "benzene phase" formed, which were separated by phase separation.

The water phase was again introduced into the reactor together with fresh benzene (50 g benzene/100 g waterphase). The mixture was again stirred for 15 minutes and subsequently separated into two phases. This extraction step with benzene was repeated two additional times. The resulting "four benzene phases" were mixed with fresh water (25 g/100 g benzene phase). This mixture was stirred for 15 minutes and subsequently separated into two phases.

This water extraction was repeated two additional times. The resulting water phases from the benzene extraction and the water phases obtained from the water extraction were mixed together. The resulting mixture was concentrated by evaporation to a lactam concentration of 33 wt. %.

The resulting mixture was hydrogenated in the same manner as described in Example I. After the separation of the hydrogenation catalyst, the mixture was contacted with a cationic exchanger (DOWEX 50) and subsequently with an anionic exchanger (DOWEX 21K.), 1 ml of ion exchanger per 10 ml water/ε-caprolactam mixture was used. The ion exchanger was placed in a column and the water/ε-caprolactam mixture was passed over the packed-bed.

The resulting mixture was distilled in the same manner as described in Example I. The properties of the distilled ε-caprolactam are shown in Table 3. The ε-caprolactam was of a purity and quality such that it could be reused directly in the manufacture of nylon-6 fibers or other nylon-6 products without the need to blend the ε-caprolactam thus obtained with virgin ε-caprolactam obtained by Beckmann rearrangement or any other known synthetic method of preparation.

Comparative Experiment D

The mixture to be purified from Example III was concentrated by evaporation to a lactam concentration of 70 wt. %.

70 g of this mixture was stirred for 15 min together with 9.3 g of 3% by weight aqueous potassium permanganate solution at 40° C. and a pH of 7.0. The pH was kept at 7.0 during the oxidation by the addition of 1.0N sulphuric acid. The manganese dioxide ($MnO_2$) formed was then removed from the reaction product by means of pressure filtration. The filtration time was 60 min. The filter cake, composed of dry manganese dioxide, weighed 1.7 g.

3.5 ml of 1.5N aqueous sodium hydroxide solution was added to the mixture. This mixture was then distilled by reducing the pressure in steps. Lactam was distilled at approximately 1–1.5 mm Hg. The properties of the distilled ε-caprolactam are shown in Table 3.

TABLE 3

|  | III | D |
|---|---|---|
| °Hazen (ISO 8112) | 2 | 5 |
| PM number | >10,000 | 2000 |
| Abs 290 (ISO 7059) | 0.16 | 2.5 |
| Alkalinity V1 bases (ISO 8661) | 0.04 | — |
| (ISO 8661) | 0.38 | — |
| PAN (ISO 8660) | 3.6 | 8.5 |

While the present invention has been described in connection with what is presently considered to be the most practical and preferred embodiments, it is to be understood that the invention is not to be limited to the disclosed embodiments, but on the contrary is intended to cover various modifications and equivalents included within the spirit and scope of the appended claims.

What is claimed is:

1. A method of purifying ε-caprolactam from carpet waste containing nylon-6, comprising the steps of:
   a) separating carpet waste containing nylon-6 to obtain a fraction containing nylon-6;
   b) depolymerizing said fraction containing nylon-6 obtained in step a) to obtain contaminated ε-caprolactam; and
   c) hydrogenating a mixture of water and said contaminated ε-caprolactam in the presence of hydrogen and hydrogenation catalyst in order to obtain purified ε-caprolactam; and
   d) recovering said purified ε-caprolactam from said mixture.

2. The method of claim 1, wherein the amount of said contaminated ε-caprolactam in said mixture is between about 10 and about 95% by weight.

3. The method of claim 1, wherein said mixture is first saturated with hydrogen and subsequently contacted with a heterogeneous hydrogenation catalyst.

4. The method of claim 1, wherein said carpet waste is mechanically separated into nylon-6 containing carpet material and non-nylon-6 containing carpet material prior to said depolymerizing step.

5. The method of claim 1 wherein said depolymerization of nylon-6 is performed in the presence of phosphoric acid.

6. The method of claim 1, wherein said carpet waste comprises post-consumer nylon-6 containing carpet.

7. A method of separating ε-caprolactam, from carpet waste containing nylon-6, comprising the steps of:
   a) separating carpet waste containing nylon-6, so as to provide a fraction containing nylon-6;
   b) depolymerizing the fraction containing nylon-6 obtained in step a) in order to obtain contaminated ε-caprolactam;
   c) hydrogenating a mixture of water and said contaminated ε-caprolactam in the presence of hydrogen and a hydrogenation catalyst in order to obtain purified ε-caprolactam;
   d) recovering said purified ε-caprolactam from said mixture;
   e) subjecting said mixture to ion exchange treatment in order to obtain further purified ε-caprolactam;
   f) distilling said further purified ε-caprolactam and
   g) recovering said further purified ε-caprolactam.

8. The method of claim 7, wherein the amount of said contaminated ε-caprolactam in said mixture is between about 10 and about 95% by weight.

9. The method of claim 7, wherein said mixture is first saturated with hydrogen and subsequently contacted with a heterogeneous hydrogenation catalyst.

10. The method of claim 7, wherein said carpet waste is mechanically separated into nylon-6 and non-nylon-6 containing carpet prior to said depolymerizing step.

11. The method of claim 7, wherein said depolymerization of nylon-6 is performed in the presence of phosphoric acid.

12. The method of claim 7, wherein said carpet waste comprises post-consumer nylon-6 containing carpet.

13. A method of purifying ε-caprolactam from carpet waste containing nylon-6 which consists essentially of the combination of steps of:
   a) separating carpet waste containing nylon-6 to obtain a fraction containing nylon-6;
   b) depolymerizing said fraction containing nylon-6 obtained in step a) to obtain contaminated ε-caprolactam; and
   c) hydrogenating a mixture of water and said contaminated ε-caprolactam in the presence of hydrogen and a hydrogenation catalyst in order to obtained purified ε-caprolactam; and
   d) recovering said purified ε-caprolactam from said mixture.

14. The method of claim 13, wherein said method includes the further steps (e), (f) and (g):
   e) subjecting said mixture to ion exchange treatment in order to obtain further purified ε-caprolactam;
   f) distilling said further purified ε-caprolactam and
   g) recovering said further purified ε-caprolactam.

* * * * *